(12) United States Patent
Fraz et al.

(10) Patent No.: US 10,796,140 B2
(45) Date of Patent: Oct. 6, 2020

(54) METHOD AND APPARATUS FOR HEALTH AND SAFETY MONITORING OF A SUBJECT IN A ROOM

(71) Applicant: Oxehealth Limited, Oxford (GB)

(72) Inventors: Muhammad Fraz, Oxford (GB); Simon Mark Chave Jones, Oxford (GB); Luke Marcus Biagio Testa, Oxford (GB)

(73) Assignee: OXEHEALTH LIMITED, London (GB)

( * ) Notice: Subject to any disclaimer, the term of this patent is extended or adjusted under 35 U.S.C. 154(b) by 118 days.

(21) Appl. No.: 16/071,591

(22) PCT Filed: Jan. 19, 2017

(86) PCT No.: PCT/GB2017/050127
§ 371 (c)(1),
(2) Date: Jul. 20, 2018

(87) PCT Pub. No.: WO2017/125743
PCT Pub. Date: Jul. 27, 2017

(65) Prior Publication Data
US 2019/0034713 A1    Jan. 31, 2019

(30) Foreign Application Priority Data
Jan. 21, 2016    (GB) .................................. 1601143.9

(51) Int. Cl.
*G06K 9/00* (2006.01)
*G06T 7/20* (2017.01)
(Continued)

(52) U.S. Cl.
CPC ........ *G06K 9/00342* (2013.01); *A61B 5/0205* (2013.01); *A61B 5/1128* (2013.01);
(Continued)

(58) Field of Classification Search
CPC . A61B 5/02416; A61B 5/1128; A61B 5/0205; A61B 5/746; A61B 5/1115;
(Continued)

(56) References Cited

U.S. PATENT DOCUMENTS 8,855,384 B2   10/2014   Kyal et al.
8,965,090 B1   2/2015    Khachaturian et al.
(Continued)

FOREIGN PATENT DOCUMENTS

EP    0615245 A2    9/1994
EP    0919184 A1    6/1999
(Continued)

OTHER PUBLICATIONS

Nakajima, Kazuki, Yoshiaki Matsumoto, and Toshiyo Tamura. "Development of real-time image sequence analysis for evaluating posture change and respiratory rate of a subject in bed." Physiological Measurement 22.3 (2001).*

(Continued)

*Primary Examiner* — Li Liu
(74) *Attorney, Agent, or Firm* — Harness, Dickey & Pierce, P.L.C.

(57) ABSTRACT

A method and apparatus for monitoring the health and safety of a subject in a room such as a secure room based on video images of the subject. The images are analysed to characterise the movement of the subject as gross movement, fine movement or no movement. In the case of gross movement, no vital signs of the subject are estimated and a display indicates that the subject is moving, but no vital signs are available. In the absence of gross movement, vital signs of the subject such as heart rate or breathing rate are estimated from the video images of the subject, for example by detecting and analysing photoplethysmogram signals in the video images, and the vital signs are displayed. Alerts may (Continued)

be generated if the vital signs are out of the normal physiological range. If vital signs cannot be detected in the video images but the movement of the subject is characterised as fine movement, the display shows that no vital signs are being estimated, but that the subject is moving. If no movement is detected and no vital signs estimate is obtained, then the display generates an alert indicating lack of movement and lack of vital signs.

6 Claims, 2 Drawing Sheets

(51) Int. Cl.
| | |
|---|---|
| A61B 5/11 | (2006.01) |
| G08B 21/04 | (2006.01) |
| A61B 5/00 | (2006.01) |
| A61B 5/0205 | (2006.01) |
| G06T 7/246 | (2017.01) |
| G06T 7/73 | (2017.01) |
| G06T 7/00 | (2017.01) |
| A61B 5/08 | (2006.01) |
| A61B 5/024 | (2006.01) |

(52) U.S. Cl.
CPC .......... *A61B 5/746* (2013.01); *G06K 9/00771* (2013.01); *G06T 7/20* (2013.01); *G06T 7/246* (2017.01); *G06T 7/73* (2017.01); *G06T 7/97* (2017.01); *G08B 21/0476* (2013.01); *A61B 5/02416* (2013.01); *A61B 5/0816* (2013.01); *A61B 5/1116* (2013.01); *A61B 5/4094* (2013.01); *A61B 5/7264* (2013.01); *G06K 2009/00939* (2013.01); *G06T 2207/10016* (2013.01); *G06T 2207/10024* (2013.01); *G06T 2207/10048* (2013.01); *G06T 2207/30196* (2013.01); *G06T 2207/30232* (2013.01); *G08B 21/0415* (2013.01)

(58) Field of Classification Search
CPC ....... A61B 2576/00; A61B 5/11; A61B 5/742; G06T 2207/10016; G06T 2207/30076; G06T 7/20; G06T 2207/30196; G06T 2207/30232; G06T 7/0016; G06K 9/00771; G06K 2009/00939; G06K 9/00261; G06K 9/00342; G06K 2009/00738
See application file for complete search history.

(56) References Cited

U.S. PATENT DOCUMENTS

| | | | |
|---|---|---|---|
| 9,036,877 B2 | 5/2015 | Kyal et al. | |
| 10,034,979 B2 * | 7/2018 | Bechtel | A61B 5/7275 |
| 10,292,662 B2 * | 5/2019 | Kirenko | A61B 5/7214 |
| 2002/0106709 A1 | 8/2002 | Potts et al. | |
| 2002/0180870 A1 | 12/2002 | Chen | |
| 2003/0138149 A1 | 7/2003 | Iizuka et al. | |
| 2003/0228032 A1 | 12/2003 | Rui et al. | |
| 2005/0197590 A1 | 9/2005 | Osorio et al. | |
| 2006/0058618 A1 | 3/2006 | Nishiura | |
| 2007/0195931 A1 | 8/2007 | Ohishi | |
| 2008/0292151 A1 * | 11/2008 | Kurtz | A61B 3/10 |
| | | | 382/128 |
| 2009/0216499 A1 | 8/2009 | Tobola et al. | |
| 2010/0049064 A1 | 2/2010 | Bodmer et al. | |
| 2010/0074475 A1 | 3/2010 | Chouno | |
| 2010/0298656 A1 * | 11/2010 | McCombie | G16H 50/50 |
| | | | 600/301 |
| 2011/0046498 A1 * | 2/2011 | Klap | A61B 5/0205 |
| | | | 600/534 |
| 2011/0150274 A1 | 6/2011 | Patwardhan et al. | |
| 2011/0251493 A1 | 10/2011 | Poh et al. | |
| 2011/0311143 A1 | 12/2011 | Cennini et al. | |
| 2012/0141000 A1 * | 6/2012 | Jeanne | G06K 9/00496 |
| | | | 382/128 |
| 2012/0213405 A1 | 8/2012 | Sasaki | |
| 2012/0242819 A1 | 9/2012 | Schamp | |
| 2013/0138009 A1 | 5/2013 | Nierenberg et al. | |
| 2013/0324875 A1 | 12/2013 | Mestha et al. | |
| 2014/0003690 A1 | 1/2014 | Razeto et al. | |
| 2014/0023235 A1 | 1/2014 | Cennini et al. | |
| 2014/0037163 A1 | 2/2014 | Kirenko et al. | |
| 2014/0037166 A1 | 2/2014 | De Haan et al. | |
| 2014/0236036 A1 | 8/2014 | de Haan et al. | |
| 2014/0276099 A1 | 9/2014 | Kirenko et al. | |
| 2014/0276104 A1 | 9/2014 | Tao et al. | |
| 2014/0334697 A1 | 11/2014 | Kersten et al. | |
| 2014/0371599 A1 | 12/2014 | Wu et al. | |
| 2014/0371635 A1 * | 12/2014 | Shinar | A61B 5/6891 |
| | | | 600/595 |
| 2014/0378842 A1 | 12/2014 | Xu et al. | |
| 2015/0005646 A1 | 1/2015 | Balakrishnan et al. | |
| 2015/0063708 A1 | 3/2015 | Sripadarao et al. | |
| 2015/0148687 A1 | 5/2015 | Kitajima et al. | |
| 2015/0208987 A1 | 7/2015 | Shan et al. | |
| 2015/0221069 A1 | 8/2015 | Shaburova et al. | |
| 2015/0250391 A1 | 9/2015 | Kyal et al. | |
| 2015/0363361 A1 | 12/2015 | Kniazev | |
| 2016/0106340 A1 | 4/2016 | Mestha et al. | |
| 2016/0125260 A1 | 5/2016 | Huang et al. | |
| 2016/0132732 A1 | 5/2016 | Gunther et al. | |
| 2016/0220128 A1 | 8/2016 | Den Brinker et al. | |
| 2016/0253820 A1 * | 9/2016 | Jeanne | A61B 5/7207 |
| | | | 382/107 |
| 2016/0310067 A1 | 10/2016 | Heinrich et al. | |
| 2017/0007185 A1 | 1/2017 | Lin et al. | |
| 2017/0042432 A1 | 2/2017 | Adib et al. | |
| 2017/0224256 A1 | 8/2017 | Kirenko | |
| 2017/0238805 A1 | 8/2017 | Addison et al. | |
| 2017/0238842 A1 | 8/2017 | Jacquel et al. | |
| 2018/0085010 A1 | 3/2018 | Jones et al. | |
| 2018/0279885 A1 * | 10/2018 | Bulut | A61B 5/7275 |
| 2019/0000391 A1 * | 1/2019 | De Haan | A61B 5/02433 |
| 2019/0267040 A1 | 8/2019 | Ikeda et al. | |

FOREIGN PATENT DOCUMENTS

| | | |
|---|---|---|
| EP | 1571594 A2 | 9/2005 |
| EP | 2767233 A1 | 8/2014 |
| EP | 2976998 A1 | 1/2016 |
| EP | 2988274 A2 | 2/2016 |
| EP | 3073905 A1 | 10/2016 |
| EP | 3207862 A1 | 8/2017 |
| JP | 2011130996 A | 7/2011 |
| WO | WO-2010/100593 A1 | 9/2010 |
| WO | WO-2010/115939 A2 | 10/2010 |
| WO | WO-2011/021128 A2 | 2/2011 |
| WO | WO-2013/027027 A2 | 2/2013 |
| WO | WO-2014125250 A1 | 8/2014 |
| WO | WO-2014131850 A1 | 9/2014 |
| WO | WO-2014140994 A1 | 9/2014 |
| WO | WO-2015/049150 A1 | 4/2015 |
| WO | WO-2015/055709 A1 | 4/2015 |
| WO | WO-201504915 A1 | 4/2015 |
| WO | WO-2015/078735 A1 | 6/2015 |
| WO | WO-2015/091582 A1 | 6/2015 |
| WO | WO-2015086414 A1 | 6/2015 |
| WO | WO-2015172735 A1 | 11/2015 |
| WO | WO-2016092290 A1 | 6/2016 |
| WO | WO-2016094749 A1 | 6/2016 |
| WO | WO-2016159151 A1 | 10/2016 |
| WO | WO-2017125743 A1 | 7/2017 |
| WO | WO-2017125744 A1 | 7/2017 |
| WO | WO-2017125763 A1 | 7/2017 |

OTHER PUBLICATIONS

Pisani-Real-time Automated Detection of Clonic Seizures in Newborns, Clinical Neurophysiology 125 (2014) 1533-1540.

(56) References Cited

OTHER PUBLICATIONS

International Search Report for PCT/GB2017/050127, ISA/EP, Rijswijk, NL, dated Mar. 28, 2017.
Written Opinion of the ISA for PCT/GB2017/050127, ISA/EP, Rijswijk, NL, dated Mar. 28, 2017.
UK IPO Search Report under Section 17(5) for priority application GB1601143.9, dated Mar. 30, 2016.
Verkruysse et al., "Remote Plethysmographic imaging using ambient light", Optics Express, 16(26), Dec. 22, 2008, pp. 21434-21445.
Mayank Kumar et al, DistancePPG: Robust non-contact vital signs monitoring using a camera, Biomedical Optics Express, 2015, pp. 1565-1588.
Kumar-DistancePPG: Robust non-contact vital signs monitoring using a camera, Optical Society of America (2015).
Nathalie M. El Nabbout et al, "Automatically Detecting and Tracking People Walking through a Transparent Door with Vision", Computer and Robot Vision, 2008. CRV '08. Canadian Conference on, IEEE, Piscataway, NJ, USA, May 28, 2008 (May 28, 2008), pp. 171-178.
Qiang Zhu et al, "Learning a Sparse, Corner-Based Representation for Corner-Based Representation for Time-varying Background Modeling", Computer Vision, 2005. ICCV 2005. Tenth IEEE International Conference on Beijing, China Oct. 17-20, 2005, Piscataway, NJ, USA, IEEE, Los Alamitos, CA, USA, vol. 1, Oct. 17, 2005 (Oct. 17, 2005), pp. 678-685.
Konstantinos Avgerinakis et al, "Activity detection and recognition of daily living events", Proceedings of the 1ST ACM International Workshop on Multimedia Indexing and Information Retrieval for Healthcare, MIIRH '13, Oct. 22, 2013 (Oct. 22, 2013), pp. 1-7.
Arindam Sikdar et al, "Computer-Vision-Guided Human Pulse Rate Estimation: A Review", IEEE Reviews in Biomedical Engineering, vol. 9, Sep. 16, 2016 (Sep. 16, 2016), pp. 91-105.
Yu Sun et al,"Photoplethysmography Revisited: From Contact to Noncontact, From Point to Imaging", IEEE Transactions on Biomedical Engineering, IEEE Service Center, Piscataway, NJ, USA, vol. 63, No. 3, Mar. 1, 2016 (Mar. 1, 2016), pp. 463-477.
Tongchi Zhou et al, "A study of relative motion point trajectories for action recognition", 2015 International Conference on Wireless Communications & Signal Processing (WCSP), IEEE, Oct. 15, 2015 (Oct. 15, 2015), pp. 1-5.
Hisato Aota et al, "Extracting objects by clustering of full pixel trajectories", Signal Processing And Multimedia Applications (SIGMAP), Proceedings of the 2010 International Conference On, IEEE, Jul. 26, 2010 (Jul. 26, 2010), pp. 65-72.
Shandong Wu et al, "A hierarchical motion trajectory signature descriptor", 2008 IEEE International Conference on Robotics and Automation. The Half-Day Workshop on: Towards Autonomous Agriculture of Tomorrow, IEEE—Piscataway, NJ, USA, Piscataway, NJ, USA, May 19, 2008 (May 19, 2008), pp. 3070-3075.
Search Report for GB Application No. 1618828.6, dated Mar. 31, 2017.
International Search Report and Written Opinion for PCT/GB2017/053343, dated Jan. 4, 2018; ISA/EP.
International Search Report and Written Opinion for PCT/GB2017/052779, dated Nov. 10, 2017; ISA/EP.
Search Report for GB Application No. 1615899.0, dated Feb. 28, 2017.
International Preliminary Report on Patentability and Written Opinion regarding Applicaiton No. PCT/GB2017/052779 dated Mar. 19, 2019.
International Search Report for PCT/GB2017/050162, ISA/EP, Rijswijk, NL, dated Jul. 6, 2017.
Written Opinion of the ISA for PCT/GB2017/050162, ISA/EP, Rijswijk, NL, dated Jul. 6, 2017.
Search Report for Priority Application GB1601140.5, UK IPO, Newport, South Wales, dated Jul. 21, 2016.
International Search Report for PCT/GB2017/050128, ISA/EP, Rijswijk, NL, dated Apr. 13, 2017.
Written Opinion of the ISA for PCT/GB2017/050128, ISA/EP, Rijswijk, NL, dated Apr. 13, 2017.
Search Report under Section 17(5) for priority application GB1601142.1, UKIPO, Newport, South Wales, dated Jun. 28, 2016.
Tarassenko et al, "Non-contact video-based vital sign monitoring using ambient light and auto-regressive models", 2014 Physiol. Meas. 35 807, pp. 807-831.
Wu et al, Eulerian Video Magnification for Revealing Subtle Changes in the World, 2012.
International Search Report for PCT/GB2017/050126, ISA/EP, Rijswijk, NL, dated Apr. 20, 2017.
Written Opinion of the ISA for PCT/GB2017/050126, ISA/EP, Rijswijk, NL, dated Apr. 20, 2017.
UK IPO Search Report for GB priority application 1601217.1, Newport, South Wales, dated Jul. 25, 2016.
Search Report regarding United Kingdom Patent Application No. GB1706449.4, dated Oct. 25, 2017.
Amelard Robert et al. "Illumination-compensated non-contact imaging photoplethysmography via dual-mode temporally coded illumination". Progress in Biomedical Optics and Imaging, SPIE—International Society for Optical Engineering, Bellingham, WA, US., vol. 9316, Mar. 5, 2015.
Blocker Timon et al, "An online PPGI approach for camera based heart rate monitoring using beat-to-beat detection", 2017 IEEE Sensors Applications Symposium (SAS), IEEE, Mar. 13, 2017.
Extended European Search Report regarding applicaiton No. 18168310.3-1115 dated Oct. 1, 2018.
European Search Report regarding Application No. EP 19 15 8085 dated Jul. 10, 2019.
Search Report of UKIPO regarding Application No. GB1900033.0 dated Jun. 13, 2019.
British Search Report regarding Appliction No. 1900034.8 dated Jun. 13, 2019.
Extended EP Search Report regarding Application No. 19220090.5 dated Feb. 24, 2020.
U.S. Appl. No. 16/732,769, filed Jan. 2, 2020, Nicholas Dunkley Hutchinson.
U.S. Appl. No. 16/732,979, filed Jan. 2, 2020, Nicholas Dunkley Hutchinson.
U.S. Appl. No. 16/733,065, filed Jan. 2, 2020, Nicholas Dunkley Hutchinson.
U.S. Appl. No. 15/961,279, filed Apr. 24, 2018, Nicholas Dunkley Hutchinson.
U.S. Appl. No. 16/071,542, filed Jul. 20, 2018, Nicholas Dunkley Hutchinson.
U.S. Appl. No. 16/071,570, filed Jul. 20, 2018, Simon Mark Chave Jones.
U.S. Appl. No. 16/071,611, filed Jul. 20, 2018, Nicholas Dunkley Hutchinson.
U.S. Appl. No. 16/291,728, filed Mar. 4, 2019, Nicholas Dunkley Hutchinson.
U.S. Appl. No. 16/334,211, filed Mar. 18, 2019, Mohamed Elmikaty.
U.S. Appl. No. 16/347,925, filed May 7, 2019, Simon Mark Chave Jones.

* cited by examiner

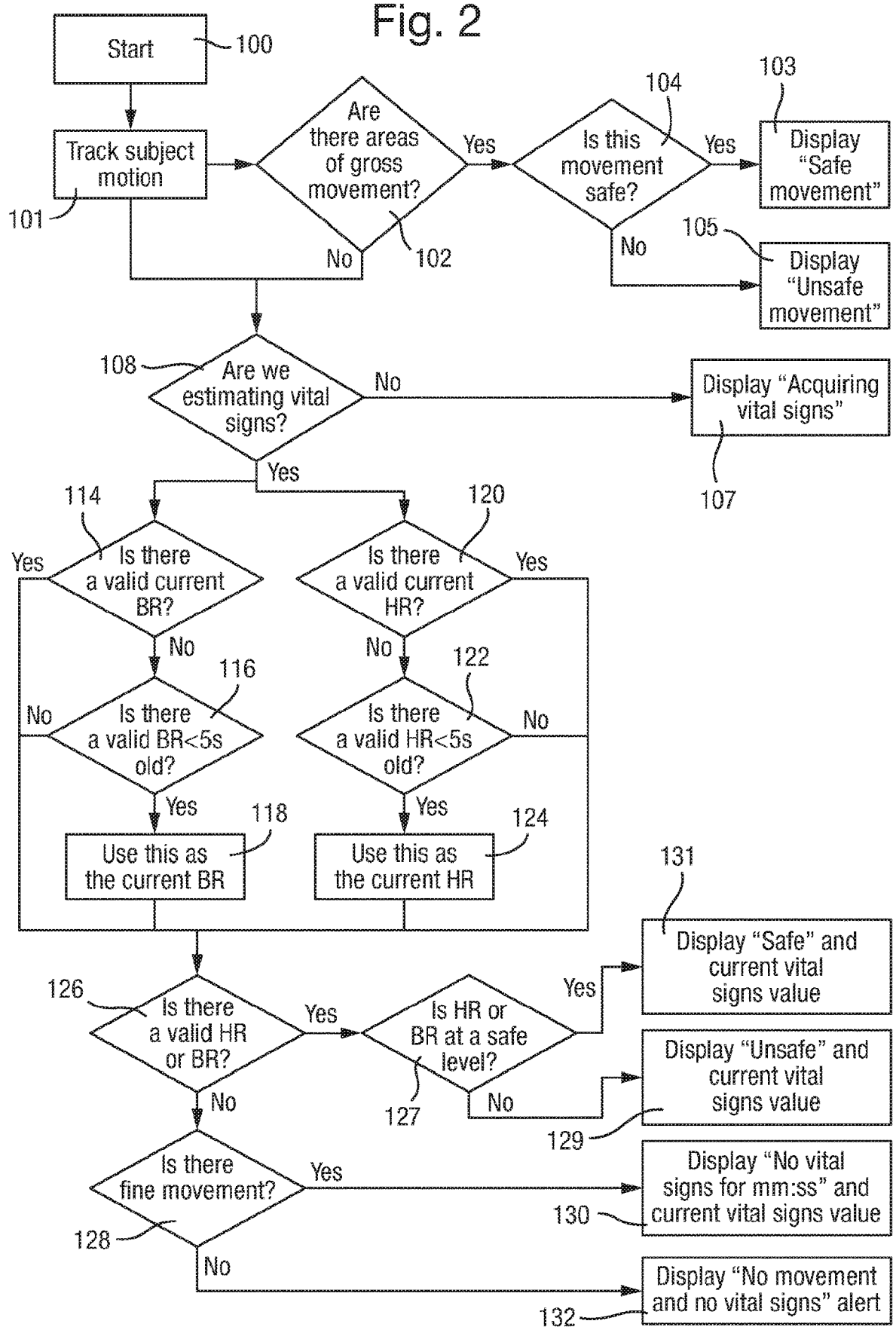

METHOD AND APPARATUS FOR HEALTH AND SAFETY MONITORING OF A SUBJECT IN A ROOM

CROSS-REFERENCE TO RELATED APPLICATIONS

This application is a 371 U.S. National Stage of International Application No. PCT/GB2017/050127, filed Jan. 19, 2017, which claims priority to British Patent Application No. 1601143.9, filed Jan. 21, 2016. The entire disclosures of the above applications are incorporated herein by reference.

The present invention relates to a method and apparatus for monitoring and outputting an indication of the health and safety of a subject in a room, and in particular a subject detained in an enclosed room such as a secure room.

There are many situations where a subject is in an enclosed environment, such as a room in a hospital, secure room in a prison or hospital, or even a home environment, where a duty of care is placed on an authority responsible for the subject. To comply with such duty of care requirements, it is conventional to monitor subjects in such environments. Such monitoring may comprise regular, scheduled visual checks by a member of staff and/or continuous video monitoring of the subject in the room. While such monitoring can be effective, difficulties can arise with the subject's health changing quickly between scheduled checks, or with a lack of movement of the subject being misinterpreted. For example, a subject who is lying still on a bed or on the floor may be resting or asleep, or may have a suffered a deterioration in health. Subjects who are under the influence of alcohol or drugs or suffering a mental condition may behave in ways which are abnormal and difficult for staff observing them to interpret correctly. It would therefore be useful to have a way of monitoring the subject which provides an indication of their health.

Monitoring of vital signs offers the possibility of mitigating some of these problems, but traditional contact-based vital signs sensors are restrictive and inconvenient, and some subjects may not co-operate with their use. Recent developments demonstrating that vital signs such as heart rate or breathing rate can be detected in video images of the human body, where the video images are obtained using a standard video camera, are of significant interest. For example Verkruysse et al., "Remote plethysmographic imaging using ambient light", Optics Express, 16 (26), 22 Dec. 2008, PP. 21434-21445 demonstrated that photoplethysmographic signals could be detected in the video signal from a conventional consumer standard video camera where a human subject was illuminated under ambient light. This idea has been developed further in, for example, WO-A2-2013/027027, WO-A-2011/021128 and WO-A1-2015/049150 which aim to increase the reliability of the detection of the remote PPG signal.

The paper "Distance PPG: robust non-contact vital signs monitoring using a camera" by Mayank Kumar et al.; 6 Apr. 2015; Biomedical Optics Express 1565, 1 May 2015, Vol. 6 No. 5, discusses a method of combining skin-colour change signals from different tracked regions of a subject's face using a weighted average, where the weights depend on the blood perfusion and incident light density in the region to improve the signal-to-noise ratio of the camera-based estimate. It discusses the various challenges for camera-based non-contact vital sign monitoring and proposes that improvements in the signal-to-noise ratio of the camera-based estimates reduces the errors in vital sign estimation.

Many of the prior art techniques have been based on careful control of the subject being monitored and the lighting conditions in the environment. Thus, although they claim success in detecting the heart rate or vital signs of the subject, in general the subjects were required to remain relatively still, the subjects were not obscured and the lighting conditions were kept relatively constant. It would be useful to be able to detect vital signs, in particular heart and/or breathing rate, of subjects in a wide variety of settings where the subject and environment may be less controlled. For example, being able to monitor a subject in a room such as a secure room, but able to freely move within the room would be useful, but is much more difficult. In real life subjects mix periods of high activity and large movement with periods of relative immobility (seated or lying), will in general be clothed and have bedding to cover themselves. Thus, periods of inactivity while lying down, may coincide with the subject covering themselves partly or completely (known as "tenting") with bedding. Further, illumination may vary between daylight and artificial light and secure rooms are sometimes lit with visible artificial light and are sometimes completely dark, with infrared being the only illumination available. Existing systems do not provide vital signs monitoring such as heart or breathing rate detection which can operate reliably in the face of these difficulties. Similar problems of movement and variable illumination occur also in other fields such as fitness and health and well-being in the home or elsewhere. Being able to monitor a subject in these less controlled conditions and provide practically useful information would significantly improve the ability to monitor the well-being of such a subject and to comply with duty of care requirements, particularly in the security field. As with all monitoring systems, the primary need is to avoid excessive false alarming and also to avoid excessive under alarming. Excessive false alarming leads to monitoring systems being ignored by staff, or switched off. Excessive under alarming leads to a lack of trust in the system and does not meet the basic requirements of the monitoring system.

SUMMARY OF THE INVENTION

The present invention therefore provides a method and apparatus which allows safe monitoring of a subject by giving an indication of the subject's vital signs where these are available, or providing useful information where the vital signs are of lower accuracy or unavailable.

Accordingly, a first aspect of the invention provides a method of monitoring a subject in a room to provide status or alerting of a subject's condition, the method comprising the steps of: capturing a video image sequence of the room using a video camera; processing the video image sequence using a data processor to automatically: measure the movement of different parts of the scene to detect areas of gross movement and fine movement; estimating one or more vital signs of the subject by analysing areas of the video image sequence not containing gross movement; and outputting an indication of the status of the subject in the room based upon both the classification of movement and the presence or absence of vital signs.

In one embodiment said step of estimating one or more vital signs is not conducted if gross movement is present in the video image sequence.

The video camera is preferably a standard digital video camera so that the video image sequence is a conventional frame sequence with each frame comprising an array of pixel intensities. The camera may be monochrome or may be a colour camera providing pixel intensities in the red, green and blue channels.

Preferably the video image sequence is time-windowed, i.e. divided into batches of successive frames for processing, and the steps of subject tracking, movement measurement and vital signs estimation are conducted on the time windows. The time windows may be of, for example, 15 frames, corresponding to 1 second. Successive time windows may be overlapping, for example by 0.9 seconds.

The estimation of vital signs of the subject may be conducted by analysing movement tracks through the video image sequence, such movement potentially including movement related to breathing or heart beat, or may comprise analysing intensity variations in particular areas of an image, such intensity variations potentially including a PPG signal.

The movement or intensity variations may be analysed to detect periodic components corresponding to breathing or heart activity and the conventional analysis techniques mentioned above can be used.

In one embodiment, if gross movement is present in the video image sequence, or the current time window under consideration, then vital signs estimation is not conducted as conventional estimation techniques will not return a reliable value in these circumstances. On the other hand the presence of gross movement means that the subject is alive and the gross movement can be further classified as representing unsafe movement or safe movement, for example detecting clonic seizures using techniques described in "Real-time automated detection of clonic seizures in newborns" by Pisani et al.

In some circumstances, even if gross movement is not present in the image, vital signs estimation algorithms do not return a reliable vital signs estimate. In this case the display is preferably controlled to indicate that no vital signs are being detected and also to indicate the time elapsed for which no estimate has been returned. Where no estimate has been made for a configurable period of time (for example 40 seconds) an alarm can be configured to be generated.

Where vital signs can be estimated, they are preferably compared to standard physiologically safe ranges, such 45 to 155 for heart rate and 6 to 30 for breathing rate, and then the display is controlled to indicate whether or not the estimated vital sign is inside or outside the physiologically safe range.

Preferably if no movement is detected and no estimate of vital signs is returned, the method further comprises displaying an alarm on the display. Optionally the alarm may also be more widely distributed, for example by pager, SMS text message, or by a combination of visible and audible alarm or by a combination of these.

The characterisation of gross movement and fine movement in the video image sequence is conducted with reference to a threshold which is preferably set in a calibration process. The aim is to distinguish deliberate or consciously performed large movements, such as a subject deliberately walking around, moving their arms, or changing position when lying or seated, from the smaller not deliberate, unconscious movements related to, for example, breathing or the cardiac cycle, such as chest rise and fall, small head movement, etc. The distance that such a gross movement or fine movement corresponds to in the individual image frames of the video image sequence depends on the field of view of the video camera and the hardware used (optics and sensor). However, a threshold which distinguishes the two types of movement can be established for any given equipment in a calibration process by capturing a video image sequence of a volunteer who is asked, on the one hand, to move deliberately, such as walking around, moving arms, or changing position when seated or lying, and on the other hand to remain as still as possible, while breathing normally. By observing the distribution of movement distances in the frames of the video image sequence in these two different states, a threshold can be set which distinguishes between them and characterises the deliberate movements as gross movement and the not deliberate movements as fine movement.

The invention extends to apparatus for monitoring a subject in a room, the apparatus comprising a video camera configured to capture a video image sequence of the subject in the room, a data processor configured to automatically process the video image as specified above, and a display for displaying the output.

The invention may also be embodied in a computer program for processing a captured video image sequence in accordance with the invention and for outputting on a display the movement characterisation and vital signs estimation (where available). Such a computer program may run on a general purpose computer of conventional type.

An embodiment of the invention provides a method and apparatus for monitoring the health and well-being of a subject in a room such as a secure room based on video images of the subject. The images are analysed to characterise the movement of the subject as gross movement, fine movement or no movement. In the case of gross movement and where no vital signs of the subject are estimated, a display indicates that the subject is moving, but no vital signs are available. In the absence of gross movement, vital signs of the subject such as heart rate or breathing rate are estimated from the video images of the subject, for example by detecting and analysing photoplethysmogram signals in the video images where there is no movement or fine movement and avoiding areas where there is gross movement, and the vital signs are displayed. Alerts may be generated if the vital signs are out of the normal physiological range. If vital signs cannot be detected in the video images but the movement of the subject is characterised as fine movement, a display is adapted to show that no vital signs are being estimated, but that the subject is moving. If no movement is detected then the display generates an alert indicating a lack of movement and lack of vital signs.

The invention thus recognises that there are types of movement of the subject which machine-vision techniques can recognise as safe; these often correspond to times when it is difficult or impossible to measure vital signs in the video image.

The invention will be further described by way of non-limitative example with reference to the accompanying drawings in which:—

FIG. 1 schematically illustrates a secure room containing a detained subject under monitoring in accordance with an embodiment of the invention;

FIG. 2 is a flow diagram explaining the process flow according to one embodiment of the invention;

Figure 1:
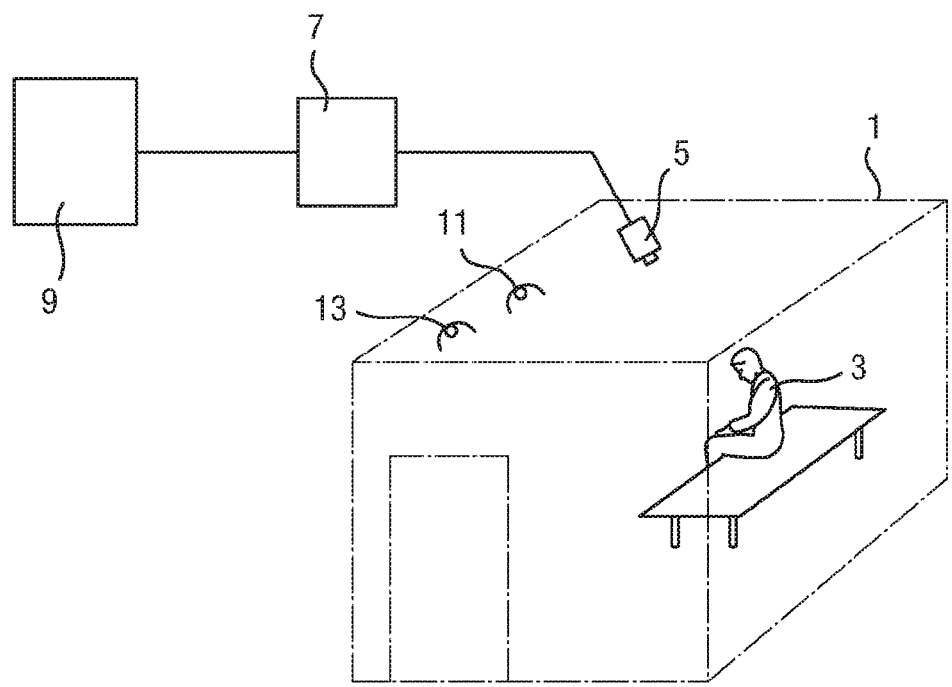

FIG. 1 schematically illustrates an apparatus in accordance with an embodiment of the invention being used to monitor a subject 3 in a room 1. The room 1 can be a secure room such as a police or prison cell or some other detention facility, or could be a room in a hospital or other care facility such as a care home, sheltered accommodation or the subject's own home. The subject 3 is monitored by a video camera 5 whose output is processed by a video signal processor 7 and the results of the analysis are displayed on a display 9 which is visible to staff of the facility. The video signal processor 7 may be a dedicated signal processor or a programmed general purpose computer. The room may be naturally lit or may be artificially illuminated using a visible light source 11 or infrared light source 13.

The video camera 5 is a standard digital video camera outputting video data in the form of a sequence of image frames, each frame being a pixel array of intensities in red, green, blue channels. The red, green and blue channels also give a response in the infrared range allowing the production of an infra-red (IR) image useful when the room is dark. Video cameras of this type typically output the signal at fifteen frames per second, though of course different frame rates are possible.

The display 9 preferably displays the video image of the room and also displays information regarding the health or safety of the subject 3. This information is preferably:—
  Whether movement is detected.
  Whether vital signs are being acquired.
  Whether the subject is judged to be safe.
  Current values of estimated vital signs such as heart rate and breathing rate.
  Whether no vital signs have been detected and the time for which no vital signs have been detected.
  A no movement and no vital signs alert or alarm.

Staff monitoring the subject by way of the display 9 can therefore tell at any given time whether the subject is considered safe, for example because they are moving or because the vital signs are being detected and are in a physiologically normal range, or whether the system is unable to detect vital signs and safe movement is detected (and for how long that situation has persisted), or that no vital signs and no movement is detected, in which case an alert is generated willing staff to check the subject. If the lack of vital signs detection persists for more than a configurable amount of time an alert may be generated to call on staff to check the subject. Alerts can included a range of electronic notification methods including automated telephone message, paper, SMS, as well as indication on the display 9 with the alert containing the condition and location of the subject and the condition being alerted.

Figure 3:
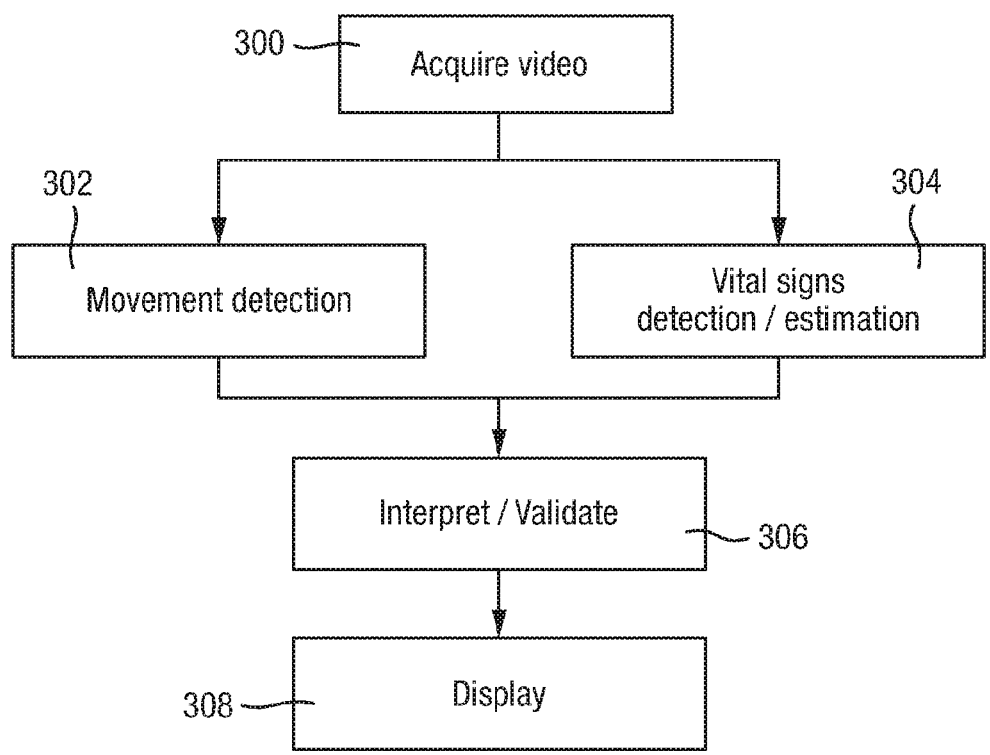
FIG. 3 illustrates the overall processing of the system of FIG. 1.

FIG. 3 schematically illustrates the overall processing. Video is acquired by camera 5 in step 300 and parallel movement detection and vital signs estimation processes 302, 304 are run. The outputs from these is interpreted and validated in step 306 and corresponding displays made in step 308.

FIG. 2 schematically illustrates in more detail how the system of the invention generates the required information for display in accordance with one embodiment of the invention. This is based on a combination of characterising the movement of the subject, together with acquisition of vital signs information such as heart rate and breathing rate from the video images of the subject.

Referring to FIG. 2, therefore, after starting in step 100, in step 101 the subject's motion is tracked through a batch of frames (for example 3 seconds) of the video sequence. The motion may be tracked by any of the well-known motion tracking techniques such as Optical Flow, Frame Differencing or Pedestrian Tracking disclosed in Cutler and L. S. Davis. Robust real-time periodic motion detection, analysis, and applications. IEEE Transactions on Pattern Analysis and Machine Intelligence, 22(8):781-796, 2000 and Bradski 2001 Motion Segmentation and Pose Recognition with Motion History Gradients.

Having tracked the subject's motion, the motion is then in step 102 assessed to determine whether there is gross movement. Gross movement is characterised as movement of the whole body, such as walking or running, or large movements of limbs, such as waving arms or legs. Gross movement thresholding would be defined differently for the different techniques but most generally will be defined as an amount of translational movement of a group of related pixels in the image. If gross movement is present then in step 104 the type of movement is assessed automatically to be classified as safe or unsafe. This can be done by using the techniques disclosed in Real-time automated detection of clonic seizures in newborns" by Pisani et al used to detect clonic seizures. If gross movement is present and is classified as safe then in step 103 a "safe movement" indication is displayed on display 9. If the gross movement is classified as unsafe, for example violent or fitting, then in step 105 a display "unsafe movement" is made on the display 9.

In step 108 it is assessed whether the processor 7 is already estimating vital signs, such as heart rate or breathing rate, by process 304. To estimate the vital signs, such as heart rate or breathing rate any of the published techniques based on analysing the image to detect a PPG signal may be used, e.g. those in WO-A2-2013/027027, WO-A-2011/021128 and WO-A1-2015/049150 or in "Distance PPG: robust non-contact vital signs monitoring using a camera" by Mayank Kumarthe which are incorporated herein by reference. These are typically based on detecting a photoplethysmogram signal in video images of the subject and deriving the heart rate and breathing rate from this PPG signal. These run in a separate parallel process 304 on the processor 7 and as they are known to the person skilled in the art are not described in detail here. If the processor 7 does not yet have enough signal data to estimate vital signs (for example because the system is starting from initialisation or because the subject has been moving grossly in an areas where vital sign estimation was previously being sensed, which means that estimation would be required to re-initialised), then in step 107 a display message "acquiring vital signs" is shown on the display 9. If in step 108 it is assessed that the processor 7 is estimating vital signs then in steps 114 and 120 it is assessed whether that parallel process is returning a valid current heart rate and breathing rate measurement. By valid, is meant within the normal physiological range for this vital sign. If there is no valid current heart rate or breathing rate then in steps 116 and 122 it is assessed whether there is a relatively recent, for example, less than 5 seconds old, valid heart rate or breathing rate estimate, and if so, then in steps 118 and 124 this will be used as the current heart rate or breathing rate.

Assuming a valid heart rate or breathing rate (either current or recent) is found, then in step 127 it is assessed whether this is at a safe physiological level. If yes, then in step 128 a "safe" message is displayed on the display 9, together with a value of the vital sign obtained (for example the heart rate or breathing rate). If the heart rate or breathing rate is not at a safe level, i.e. not physiologically normal, then in step 129 the display 9 indicates "unsafe" together with the current vital signs value, such as the actual heart rate or breathing rate. A vital sign is unsafe if it is outside the normal range of that subject, with the normal physiological range set in advance or being learnt using techniques such as disclosed in Clifton et al. "Gaussian process clustering for the functional characterisation of vital sign trajectories".

Alternatively, or in addition, the morphology of the heart beat signal can be monitored, for example using the techniques disclosed in Heart Rate Variability Features for Epilepsy Seizure Prediction by Hirotsugu Hashimoto et al.

If there is no valid heart rate or breathing rate, then in step 128 the video images are analysed to see if there is fine movement of the subject. If fine movement is detected then in step 130 it is indicated that no vital signs have been detected, and the length of time for which no vital signs have been detected. However, if no fine movement is detected in step 128 then an alert indicating that no movement is detected and no vital signs have been acquired is displayed in step 132.

Fine movement is detected by the same techniques as in steps 101 and 102 by tracking the subject's motion and comparing to a motion threshold below that used for gross movement.

The thresholds for gross and fine movement are set by parameters which are set to the size of the environment and the type of camera employed and subsequently automatically fine-tuned. Typical methods for deriving the parameters include sitting and standing still in parts of the room (fine movement) and performing gross movements such as arm waving and star-jumps (gross movement). This is because the actual threshold in terms of moved distance in the image frames depends on how much of the field of view the subject occupies in different positions in the room, which in turn depends on the field of view and the hardware specifications of the video camera (optics and sensor).

As well as providing live monitoring information the system may also provide a summary report of the vital signs and any alerts raised during predetermined periods, e.g. daily, weekly, monthly, and/or for the complete period the subject is in the room.

Although the explanation above is on the basis of a subject detained in a secure room, the same technique may be used for monitoring the health and well-being of subjects in other environments such as hospitals or care homes, the home or workplace or in fitness or health facilities such as gyms and sports facilities.

The invention may be embodied in a signal processing method, or in a signal processing apparatus which may be constructed as dedicated hardware or by means of a programmed general purpose computer or programmable digital signal processor. The invention also extends to a computer program for executing the method.

The invention claimed is:

1. A method of monitoring a subject in a room to provide status or alerting of a subject's condition, the method comprising the steps of:
capturing a video image sequence of the room using a video camera;
processing the video image sequence using a data processor to automatically:
measure the movement of different parts of the scene to detect areas of gross movement and fine movement;
estimating one or more vital signs of the subject; and
outputting an indication of the status of the subject in the room based upon both the classification of movement and the presence or absence of vital signs;
wherein said step of estimating one or more vital signs of the subject is conducted by analysing areas of the video image sequence not containing gross movement;
if said step of estimating one or more vital signs is not providing a valid heart rate or breathing rate, conducting a further step of determining whether fine movement is present in the video image sequence;
if said further step determines that fine movement is present then outputting an indication that no vital signs are detected and the length of time for which no vital signs have been detected; and
if said further step determines that fine movement is not present then outputting an alert indicating that no vital signs and no movement are detected.

2. The method according to claim 1, wherein if gross movement is detected, the gross movement is further classified as representing unsafe movement or safe movement.

3. The method according to claim 1, further comprising the step of comparing said estimate of one or more vital signs to a physiologically safe range and outputting an alert if the estimate is outside a physiologically safe range.

4. The method according to claim 1, wherein the characterisation of areas of gross movement and fine movement comprises comparing the amount of movement to a threshold set in a parameter tuning process comprising the steps of:
capturing a video image sequence of a first subject who is deliberately moving limbs of the first subject;
capturing a video image sequence of a second subject who is not deliberately moving limbs of the second subject;
measuring the amounts of movement of the limbs of the first and second subjects in the two video image sequences and setting the threshold on movement amount such that the deliberate movement is characterised as gross movement and the not deliberate movement is characterised as fine movement.

5. An apparatus for monitoring a subject in a room to provide status or alerting of a subject's condition, the apparatus comprising:
a video camera configured to capture a video image sequence of the room;
a data processor configured to automatically process the video image sequence to:
measure the movement of different parts of the scene to detect areas of gross movement and fine movement;
estimate one or more vital signs of the subject; and
a display or other output device which under the control of the data processor outputs a visible or audible indication of the classification of movement and an indication of the detection of the vital signs, wherein the data processor is adapted to estimate one or more vital signs by analysing areas of the video image sequence not containing gross movement;
if said step of estimating one or more vital signs is not providing a valid heart rate or breathing rate, to conduct a further step of determining whether fine movement is present in the video image sequence;
if said further step determines that fine movement is present then to output an indication that no vital signs are detected and the length of time for which no vital signs have been detected; and
if said further step determines that fine movement is not present then to output an alert indicating that no vital signs and no movement are detected.

6. A non-transitory computer readable medium having stored thereon software instructions that, when executed by a processor, cause the processor to generate a processing of a captured video image sequence of a subject in a room to automatically:
measure the movement of different parts of the scene to detect areas of gross movement and fine movement;
estimate one or more vital signs of the subject by analysing areas of the video image sequence not containing gross movement; and
outputting an indication of the status of the subject in the room based upon both the classification of movement and the presence or absence of vital signs, wherein said step of estimating one or more vital signs is conducted by analysing areas of the video image sequence not containing gross movement;

if said step of estimating one or more vital signs is not providing a valid heart rate or breathing rate, conducting a further step of determining whether fine movement is present in the video image sequence;

if said further step determines that fine movement is present then outputting an indication that no vital signs are detected and the length of time for which no vital signs have been detected; and if said further step determines that fine movement is not present then outputting an alert indicating that no vital signs and no movement are detected.

* * * * *